United States Patent [19]

Neef et al.

[11] Patent Number: 4,843,157

[45] Date of Patent: Jun. 27, 1989

[54] 13ALPHA-ALKYLGONAN-DELTA 9(11)-5,10-EPOXIDES

[75] Inventors: Guenter Neef; Harry Vierhufe, both of Berlin, Fed. Rep. of Germany

[73] Assignee: Schering Aktiengesellschaft, Berlin and Bergkamen, Fed. Rep. of Germany

[21] Appl. No.: 91,247

[22] Filed: Aug. 31, 1987

[30] Foreign Application Priority Data

Sep. 1, 1986 [DE] Fed. Rep. of Germany ....... 3630030

[51] Int. Cl.$^4$ .............................................. C07J 71/00
[52] U.S. Cl. ..................................................... 540/76
[58] Field of Search .......................................... 540/76

[56] References Cited

U.S. PATENT DOCUMENTS 3,053,839  9/1962  Iriarte et al. ......................... 540/76
3,697,511  10/1972  Bucourt et al. ....................... 540/76
4,257,948  3/1981  Costerousse et al. ................. 540/76

FOREIGN PATENT DOCUMENTS 0129499  12/1984  European Pat. Off. .
0245170  11/1987  European Pat. Off. .
1550974  7/1970  France .

OTHER PUBLICATIONS

"Stereoselective Epoxidation of 5(10,9(11)-Estradienes", Tetrahedr on Letters, vol. 26, No. 17, pp. 2069-2072 (1985) by Ralph Rohde et al.

Primary Examiner—Leonard Schenkman
Assistant Examiner—Joseph A. Lipovsky
Attorney, Agent, or Firm—Millen & White

[57] ABSTRACT

13alpha-alkylgonan-delta$^{9(11)}$-5,10 epoxides of the formula

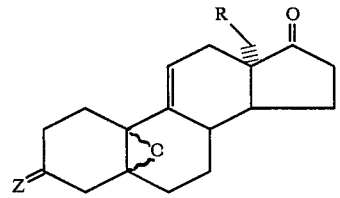

in which
R is a hydrogen, methyl or ethyl and
Z is a ketal or thioketal group effective as a keto-blocking group, are provided by a process wherein a compound of the formula

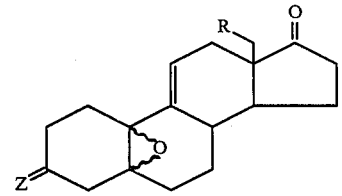

in which R and Z are as defined above, is irradiated with active ultraviolet radiation.

16 Claims, No Drawings

13ALPHA-ALKYLGONAN-DELTA 9(11)-5,10-EPOXIDES

BACKGROUND OF THE INVENTION

This invention relates to novel 13alpha-alkylgonan-delta[9(11)]-5,10-epoxides and to a method for their preparation.

11beta-Aryl-substituted 13alpha-alkylgonans are known to be effective antigestagens and antiglucocorticoids (Steroids 44, 349 [1984], European Patent Application, Publication No. 0129 499).

In the process used up to now, their production takes place via an 11beta-aryl substituted 13alpha-alkyl-5alpha-hydroxy-17-oxo-gonan intermediate product. By nucleophilic addition of a side chain on the 17-ketone, optional variation of the C-17 substituent pattern, and then splitting off of water with simultaneous cleavage of the protecting groups present, the intermediate is converted in each case into the desired end product. A serious disadvantage of this process is the occurrence of nonstereoselective introduction of the C-17 side chain into the steroid skeleton. As a result, a yield-reducing and mostly very expensive separation of the two epimers becomes necessary.

SUMMARY OF THE INVENTION it is therefore an object of this invention to provide intermediate products, which yield, stereoselectively, only the desired side chain isomers, and to provide a process for their production and for using them to prepare the desired end products.

Upon further study of the specification and appended claims, further objects and advantages of this invention will become apparent to those skilled in the art.

In one aspect of the invention, these objects have been attained by providing compounds of the formula:

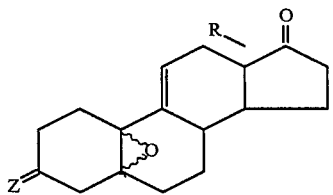
(I)

wherein
R signifies a hydrogen atom, or a methyl or ethyl group and
Z signifies a keto group blocked in the form of a ketal or thioketal, e.g., suitable for performing the subsequent reactions discussed herein.

In another aspect, these objects have been attained by providing a process for production of 13alpha-alkylgonan-delta[9(11)]-5,10 epoxides of formula I, wherein R and Z have the meanings given above, comprising irradiating a compound of the formula

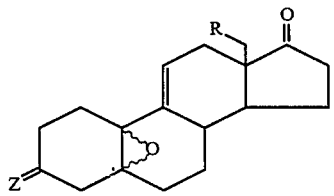
(II)

in which R and Z have the meanings given above, with ultraviolet light.

Suitable protecting groups Z include groups easily cleavable in an acid medium such as, for example, ethylenedioxyketal, ethylenedithioketal or a 2,2-dimethyl-trimethylenedioxyketal group. Other suitable blocking groups, e.g., okathiolanes, are known and disclosed, for example, in *Protective Groups in Organic Synthesis*, p. 114, Greene, T. W., John Wiley & Sons, New York (1981).

In the production of the new 13alpha-alkylgonan-delta[9(11)]-5,10 epoxides of Formula I according to the invention, the starting materials of Formula II can be prepared, for example, according to Tetrahedron Letters 26, 2069 (1985). These are connected to their 13alpha epimers by irradiation with ultraviolet radiation.

The photochemical conversion in this case is preferably performed in a conventional immersion apparatus or by means of a conventional falling-film photoreactor, and a conventional mercury high-pressure lamp is used as the radiation source. Such apparatus comprise quartz glass or special conventional glasses·of suitable spectral transparency. The reaction is conducted in a solvent. Preferred solvents are nonpolar aprotic solvents such as hexane, cyclohexane, benzene, toluene, tetrahydrofuran, dioxane or mixtures thereof. Suitable radiation periods are in the range of from 1 to 4 hours. Preferred radiation wavelengths are in the range of from about 250 to about 350 nm.

A suitable temperature range is $-30°$ to $+30°$ C.

The products of Formula I can be conventionally purified by crystallization or preferably by chromatography. Suitable concentrations of the solvents used during the irradiation step are in the range of from 0.5 to 3.0% by weight based on the total weight of the system. The achieved yields are in the range of 45 to 60%.

By the process according to the invention the new intermediate products of Formula I are obtained, which, in the subsequent nucleophilic addition of the C-17 side chain, yield exclusively the desired alpha-hydroxy epimers. This is demonstrated by way of example in the preparation of 3,3-(2,2-dimethyl-trimethylenedioxy)-5alpha,10alpha-epoxy-13alpha-methyl-17beta-[3-(tetrahydropyran-2-yloxy)-prop-1-inyl]-9(11)-gonen-17alpha-ol, described below.

A solution of 13.5 g of propargyl-THP ether in 160 ml of absolute tetrahydrofuran is mixed by instillation at 0° C. with 76.7ml of a 1.6-molar solution of n-butyllithium in hexane. It is further stirred for 15 minutes at 0° C., then cooled to $-20°$ C. and then a solution of 4.91 g of the 3,3-(2,2-dimethyl-trimethylenedioxy)-5alpha,10alpha-epoxy-13alpha-methyl-gon-9(11)-en-17-one in 80 ml of absolute THF obtained according to Example 1 is instilled. After addition, it is stirred for another 60 minutes at $-20°$ C. and then poured into about 2 liters of water and extracted with ethyl acetate. After chromatography of the raw product on aluminum oxide (Merck, neutral, stage III) with hexane/ethyl acetate 5.48 g (81.1% of theory) 3,3-(2,2-dimethyl-trimethylenedioxy)-5alpha,10alpha-epoxy-13alpha-methyl-17beta-[3-(tetrahydropyran-2-yloxy)-prop-1-inyl]-9(11)-gonen-17alpha-ol is obtained as colorless oil, $^1$H-NMR (CDCl$_3$): delta =0.86 ppm (s,3H, 13alpha-CH$_3$); 0.98 (s, 3H, ketal CH$_3$); 1.05 (s,3H, ketal CH$_3$); 4.32 (dd, 2H,C=C—CH$_2$OTHP); 4.82 (m, 1H, O—CH—); 6.08 (m, 1H, H-11).

Generally, the compounds of Formula I can be reacted at the 17-position with a nucleophile, for example, as disclosed in U.S. Application Ser. No. 077,359, filed July 24, 1987.

The subsequent reactions required to prepare the preferred pharmacologically active end compounds are fully conventional.

The subsequent conventional introduction of the desired 11beta-aryl substituents takes place according to the processes described in European specifications EP 57 115 corresponding to U.S. Pat. Nos. 4,386,085; 4,447,424 and 4,519,946, or EP No. 129499 (corresponding to U.S. Application Ser. No. 810,148 filed Jan. 10, 1986; which is a C-I-P of U.S. Ser. No. 621,308, filed June 15, 1984), German specification DE 3438500 or in Steroids 44, 349 [1984]. The preparation of 11beta-(4-dimethylaminophenyl)-3,3 3-(2,2-dimethyl-trimethylenedioxy-13alpha-methyl-17beta-[3-(tetrahydropyran-2-yloxy)-prop-1-inyl]-9-gonen-5alpha,17alpha-diol, for example, can be conducted as follows:

A suspension of 630 mg of magnesium in 10 ml of absolute THF is mixed with methyl iodide and then mixed drop by drop with a solution of 5.9 g of 4-bromodimethyl aniline in 29 ml of THF, and the instillation rate is selected so that the internal temperature does not exceed 45° C. After complete dissolution of the magnesium chips, the mixture is cooled to 0° C., 132 mg of CuCl is added and stirred for 15 minutes at 0° C., before a solution of 1.17 g of the above-described propargyl adduct is instilled into 20 ml of THF. Then it is stirred for an additional 2 hours at room temperature, poured in aqueous NH$_3$ solution and extracted with ethyl acetate. After chromatography of the raw product on Al$_2$O$_3$ with hexane/ethyl acetate, 1.24 g (84.3%) of 11beta-(4-dimethylaminophenyl)-3,3-(2,2-dimethyl-trimethylenedioxy)-13alpha-methyl-17beta-[3-(tetrahydropyran-2-yloxy)-prop-1-inyl]-9-gonen-5alpha,17alpha-diol is obtained as colorless oil, identical with the product described in European patent application No. 847 300 62.1 (Publ. No. 0129 499).

The further conventional conversion to the biologically active 4,9-gonadien-3-one end product (i.e., including optional variation of the C-17 side chain, and splitting off of water with simultaneous cleavage of the protecting groups present) takes place according to the processes known in the literature (e.g., EP 129 499, EP 57 115, or Steroids 44, 349 [1984]).

These compounds are used pharmacologically according to U.S. Application Ser. No. 077,359, filed July 24, 1987.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLES

Example 1

A solution of 4.0 g of 3,3-(2,2-dimethyltrimethylenedioxy)-5alpha,10alpha-epoxy-estr-9-en-17-one in 600 ml of hexane is radiated at 25° C. for 3 hours with the full spectrum of an Hg high-pressure burner (Philips HPK 125) in a quartz glass immersion apparatus. Then the solvent is removed in a water jet vacuum and the residue is chromatographed on 700 g of aluminum oxide (Merck, neutral, stage III) with hexane/ethyl acetate. 1.96 g of 3,3-(2,2-dimethyl-trimethylenedioxy)-5alpha,10alpha-epoxy-13alpha-methyl-gon-9(11)-en-17-one is obtained as colorless oil, $^1$H-MNR (CDCl$_3$): delta=0.83 ppm (s, 3H,H-18); 1.03 (broad s, 6H, ketal CH$_3$); 5.96 (m, 1H,H-11),[$\alpha$]$_D$-31.9° (CH$_2$Cl$_2$) c=0.510).

Example 2:

A solution of 4.0 of 3,3-(2,2-dimethyltrimethylenedioxy)-5beta,10beta-epoxy-estr-9-en-17-one in 600 ml of dioxane is radiated 1.5 hours at 20° C. under the conditions of Example 1. After chromatography 1.72 g of 3,3-(2,2-dimethyl-trimethylenedioxy)-5beta,10beta-epoxy-13alpha-methyl-gon-9(11)-en-17-one is obtained as solid foam, [$\alpha$]$_D$ -119.8°(CH$_2$Cl$_2$, c=0.630), $^1$H-NMR (CDCl$_3$): delta =0.86 ppm (s, 3H, H-18);1.05 (broad s, 6H, ketal CH$_3$); 5.78 (m, 1H, H-11).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 13alpha-alkylgonan-delta$^{9(11)}$-5,10 epoxide of the formula

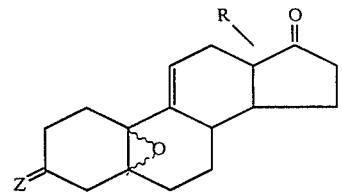

wherein
R is hydrogen, methyl or ethyl and
Z is a ketal or thioketal group effective as a keto blocking group.

2. A compound of claim 1, wherein R is hydrogen.
3. A compound of claim 1, wherein R is methyl.
4. A compound of claim 1, wherein R is ethyl.
5. A compound of claim 1, wherein Z is a ketal group.
6. A compound of claim 5, wherein Z is ethylenedioxyketal or a 2,2-dimethyltrimethylenedioxyketal group.
7. A compound of claim 1, wherein Z is a thioketal group.
8. A compound of claim 7, wherein Z is ethylenedithioketal.
9. 3,3-(2,2-dimethyl-trimethylenedioxy)-5alpha,10alpha-epoxy-13alpha-methyl-gon-9(11)-en-17-one, a compound of claim 1.
10. 3,3-(2,2-dimethyl-trimethylenedioxy)-5beta,10beta-epoxy-13alpha-methyl-gon-9(11)-en-17-one, a compound of claim 1.
11. A process for the production of a 13alphaalkylgonan-delta$^{9(11)}$-5,10 epoxide of the formula

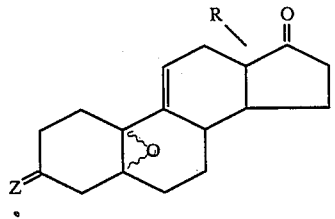

wherein

R is hydrogen, methyl or ethyl and

Z is a ketal or thioketal group effective as a keto blocking group, comprising irradiating a compound of the formula

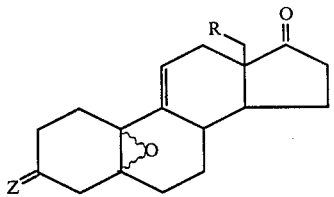

wherein
R and Z are as defined above,
  with actinic ultraviolet radiation.

12. A process of claim 11, wherein said process is conducted in from about 0.5 to about 3.0% by weight of a solvent.

13. A process of claim 12, wherein said solvent is a nonpolar, aprotic solvent.

14. A process of claim 11, wherein said process is conducted at a temperature of from about −30° C. about to +30° C.

15. A process of claim 11, wherein said process is conducted for a period of from about 1 to 4 about hours.

16. In a method of preparing a 13alpha-alkyl-5,10-epoxy gonane substituted in the 17beta- position by nucleophilic addition comprising reacting a corresponding 13alpha-alkyl-5,10-epoxy-17-keto-gonane steroid with a nucleophile, the improvement wherein said 13alpha-alkyl-5,10-epoxy-17-keto-gonane starting material is a 17-keto steroid of claim 1, whereby the resultant 17-substitution is essentially exclusively in the 17beta-position.

* * * * *

UNITED STATES PATENT AND TRADEMARK OFFICE
CERTIFICATE OF CORRECTION

PATENT NO. : 4,843,157

DATED : JUNE 27, 1989

INVENTOR(S) : NEEF ET AL

It is certified that error appears in the above-identified patent and that said Letters Patent is hereby corrected as shown below:

Column 1, formula in Summary of the Invention: should read -- lines 39-47

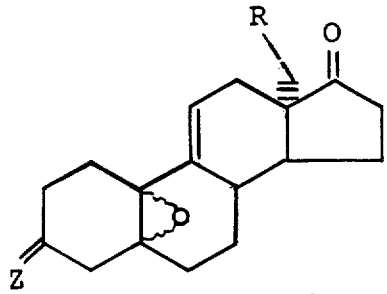

Column 4, formula in claim 1: should read --

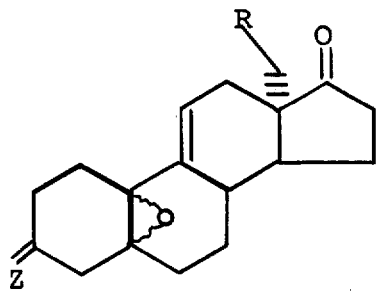

UNITED STATES PATENT AND TRADEMARK OFFICE
CERTIFICATE OF CORRECTION

PATENT NO. : 4,843,157

DATED : JUNE 27, 1989

INVENTOR(S) : NEEF ET AL

It is certified that error appears in the above-identified patent and that said Letters Patent is hereby corrected as shown below:

Column 5, formula in claim 11: should read --

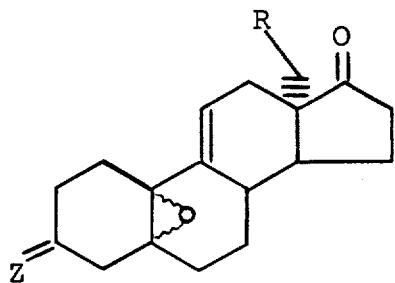

Signed and Sealed this

Twenty-ninth Day of May, 1990

Attest:

HARRY F. MANBECK, JR.

Attesting Officer

Commissioner of Patents and Trademarks